United States Patent [19]
Takechi et al.

[11] Patent Number: 5,851,451
[45] Date of Patent: Dec. 22, 1998

[54] PRODUCTION OF MICROSPHERES

[75] Inventors: Nobuyuki Takechi; Seiji Ohtani; Akihiro Nagai, all of Osaka, Japan

[73] Assignee: Takeda Chemical Industries, Ltd., Osaka, Japan

[21] Appl. No.: 766,611

[22] Filed: Dec. 13, 1996

[30] Foreign Application Priority Data

Dec. 15, 1995 [JP] Japan ................... 7-327690

[51] Int. Cl.$^6$ ............... A61K 9/16; A61K 9/50; A61K 9/52
[52] U.S. Cl. ............ 264/4.1; 264/4.33; 264/4.6; 264/4.7
[58] Field of Search ............ 264/4.1, 4.3, 4.32, 264/4.33, 4.6, 4.7

[56] References Cited

U.S. PATENT DOCUMENTS

| | | | |
|---|---|---|---|
| 4,652,441 | 3/1987 | Okada et al. | 424/19 |
| 4,954,298 | 9/1990 | Yamamoto et al. | 264/4.6 |
| 5,575,987 | 11/1996 | Kamei et al. | 424/451 |
| 5,611,971 | 3/1997 | Maedera et al. | 264/4.1 |

FOREIGN PATENT DOCUMENTS

| | | |
|---|---|---|
| 0 145 240 | 6/1985 | European Pat. Off. . |
| 0 190 833 | 8/1986 | European Pat. Off. . |
| 0 505 966 A1 | 9/1992 | European Pat. Off. . |
| 0 580 428 A1 | 1/1994 | European Pat. Off. . |

*Primary Examiner*—Nathan M. Nutter
*Attorney, Agent, or Firm*—Wenderoth, Lind & Ponack,LLP

[57] ABSTRACT

Disclosed is a method of producing microspheres which comprises subjecting a w/o/w emulsion or o/w emulsion to an in-water drying method under the following conditions:

1) the amount of microspheres per $m^3$ of an external aqueous phase is about 0.1 to about 500 kg,
2) the square root of the area (unit: $m^2$) of the liquid surface in contact with the gas phase is about 0.2 to about 4.5 per the cube root of the volume (unit: $m^3$) of an external aqueous phase,
3) the w/o/w emulsion or o/w emulsion is replaced at the replacement frequency of about 0.01 to about 10 times/minutes,
4) a gas is blown to the w/o/w emulsion or o/w emulsion at the gas transfer rate near the liquid surface of about 0.1 to about 300 m/second, and
5) the gas is replaced at the replacement frequency of not less than about 0.5 times/minutes;

and the method of the present invention increases the rate of solvent removal from microspheres in in-water drying, reduces the amount of solvent in microspheres in a short time.

14 Claims, No Drawings

PRODUCTION OF MICROSPHERES

The present invention relates to production of microspheres.

BACKGROUND OF THE INVENTION

As a prior art technology, a sustained-release preparation comprising a drug, a polylactic acid and a glycolic acid/hydroxycarboxylic acid [HOCH($C_2$–$C_8$ alkyl)COOH] copolymer is described in EP-A-481,732, for instance. As a production method for said preparation, the in-water drying method is described in which a w/o emulsion, comprising an aqueous solution of a physiologically active peptide as an internal aqueous phase and an organic solvent solution of a biodegradable polymer as an oil phase, is added to water or the like to yield a w/o/w emulsion, from which sustained-release microspheres are produced.

Also, a production of microcapsules using a water-soluble drug and a polymer by the in-water drying method is described in Japanese Patent Unexamined Publication Nos. 100516/1985 (EP-A 145240) and 201816/1987 (EP-A 190833).

In in-water drying, insufficient solvent removal, due to the unsatisfactory speed of solvent removal from microspheres, is likely to cause sphere aggregation, resulting in problems regarding the dispersibility of spheres and the needle passability during administration. An attempt to achieve sufficient solvent removal results in significantly extended in-water drying time, which in turn decreases the drug entrapment ratio in the microspheres obtained and cannot bring satisfactory results.

SUMMARY OF THE INVENTION

Through intensive investigation against this background, the present inventors found it possible to increase the speed of solvent removal from microspheres and markedly improve the drug entrapment ratio in microspheres by subjecting the microcapsules to in-water drying under particular conditions, and developed the present invention.

Accordingly, the present invention relates to a method of producing microspheres, which comprises subjecting a w/o/w emulsion or an o/w emulsion to an in-water drying method under the following conditions: ① the amount of microspheres per $m^3$ of external aqueous phase is about 0.1 to about 500 kg, ② the square root of the area (unit: $m^2$) of the liquid surface in contact with the gas phase is about 0.2 to about 4.5 per the cube root of the volume (unit: $m^3$) of an external aqueous phase, ③ the w/o/w emulsion or o/w emulsion is replaced at the replacement frequency of about 0.01 to about 10 times/minute, ④ a gas is blown to the w/o/w emulsion or o/w emulsion at the gas transfer rate near the liquid surface of about 0.1 to about 300 m/second, and ⑤ the gas is replaced at the replacement frequency of not less than 0.5 times/minute.

DETAILED DESCRIPTION OF THE INVENTION

In the present specification, abbreviations for amino acids, protecting groups and others are based on abbreviations specified by the IUPAC-IUB Commission on Biochemical Nomenclature or abbreviations in common use in relevant fields. When an optical isomer may be present in amino acid, it is of the L-configuration, unless otherwise stated.

Abbreviations used in the present specification are defined as follows:

NAcD2Nal:N-acetyl-D-3-(2-naphthyl)alanyl
D4ClPhe:D-3-(4-chlorophenyl)alanyl
D3Pal:D-3-(3-pyridyl)alanyl
NMeTyr:N-methyltyrosyl
DLys(Nic):D-(epsilon-N-nicotinoyl)lysyl
Lys(Nisp):(Epsilon-N-isopropyl)lysyl
DhArg($Et_2$):D-(N,N'-diethyl)homoarginyl Regarding weight-average molecular weight and degree of dispersion, the present specification holds that the former is in terms of polystyrene as determined by gel permeation chromatography (GPC) using 9 polystyrenes as reference substances with weight-average molecular weights of 120,000, 52,000, 22,000, 9,200, 5,050, 2,950, 1,050, 580 and 162, respectively, and that the latter is calculated therefrom. The above determination was carried out using a GPC column KF804Lx2 (produced by Showa Denko) and an RI monitor L-3300 (produced by Hitachi, Ltd.), with chloroform as a mobile phase.

Microspheres of the present invention are not limited as long as they are fine particles (microspheres) comprising a physiologically active substance (hereafter also referred to as drug) and a biodegradable polymer.

Examples of micropheres include microcapsules containing one drug core in each particle, multiple-core microcapsules containing a large number of drug cores in each particle, fine particles in which a drug in a molecular form is dissolved or dispersed in a polymer as a solid solution, etc.

Physiologically active substances include, but are not limited to, physiologically active peptides, antitumor agents, antibiotics, antipyretic agents, analgesics, anti-inflammatory agents, antitussive expectorants, sedatives, muscle relaxants, antiepileptics, antiulcer agents, antidepressants, anti-allergic agents, cardiotonics, antiarrhythmic agents, vasodilators, hypotensive diuretics, antidiabetics, antihyperlipidemic agents, anticoagulants, hemolytics, antituberculosis agents, hormones, narcotic antagonists, bone resorption suppressors, osteogenesis promoters and angiogenesis inhibitors.

The physiologically active peptide is preferably one consisting of 2 or more amino acids and having a molecular weight of about 200 to about 80,000. The physiologically active peptide is preferably LH-RH (luteinizing hormone-releasing hormone) or an analog thereof. Examples of LH-RH analogs include LH-RH agonists and LH-RH antagonists. Examples of the LH-RH agonists include a peptide represented by the formula:

$$(Pyr)Glu\text{-}R_1\text{-}Trp\text{-}Ser\text{-}R_2\text{-}R_3\text{-}R_4\text{-}Arg\text{-}Pro\text{-}R_5 \qquad (I)$$

wherein $R_1$ represents His, Tyr, Trp or p-$NH_2$-Phe; $R_2$ represents Tyr or Phe; $R_3$ represents Gly or a D-type amino acid residue; $R_4$ represents Leu, Ile or Nle; $R_5$ represents Gly-NH—$R_6$ ($R_6$ is H or an alkyl group with or without a hydroxyl group) or NH—$R_7$ ($R_7$ is H, an alkyl group with or without an amino or a hydroxyl group, or ureido (—NH—CO—$NH_2$)); [hereafter also referred to as peptide (I)] or a salt thereof.

With respect to the formula (I) above, the D-type amino acid residue in $R_3$ is exemplified by a-D-amino acids having up to 9 carbon atoms (e.g., D-Leu, Ile, Nle, Val, Nval, Abu, Phe, Phg, Ser, Thr, Met, Ala, Trp, α-Aibu). These amino acid residues may optionally have a substituent (e.g., tert-butyl, tert-butoxy, tert-butoxycarbonyl, methyl, dimethyl, trimethyl, 2-naphthyl, indoly-3-yl, 2-methyl-indolyl, benzyl-imidazo-2-yl) as appropriate.

In the formula (I), the alkyl group in $R_6$ or $R_7$ is preferably a $C_{1-4}$ alkyl group. Examples of the alkyl group include methyl, ethyl, propyl, isopropyl, butyl, isobutyl, sec-butyl and tert-butyl.

Examples of the salt of peptide (I) include acid salts (e.g., carbonate, bicarbonate, acetate, trifluoroacetate, propionate, succinate) and metal complex compounds (e.g., copper complex, zinc complex).

Peptide (I) or a salt thereof can be produced, for example, by a method which is described in U.S. Pat. Nos. 3,853,837, 4,008,209 and 3,972,859, British Patent No. 1,423,083, Proceedings of the National Academy of Science of the United States of America, Vol. 78, pp. 6509–6512 (1981), or an analogous method thereto.

Peptide (I) is preferably the following (a) to (j). (a) leuprorelin [a peptide represented by the formula (I) wherein $R_1$ is His, $R_2$ is Tyr, $R_3$ is D-Leu, $R_4$ is Leu, and $R_5$ is $NHCH_2\text{-}CH_3$];

(b) Gonadrelin

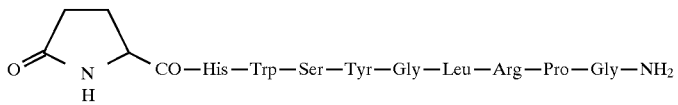

(German Patent No. 2213737);

(c) Buserelin

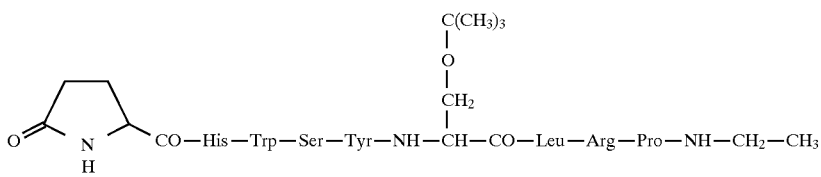

(U.S. Pat. No. 4,024,248, German Patent No. 2438352, Japanese Patent Unexamined Publication No 41359/1976);

(d) Triptorelin

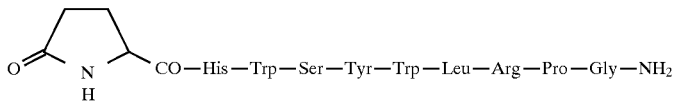

(U.S. Pat. No. 4,010,125, Japanese Patent Unexamined Publication No. 31073/1977);

(e) Goserelin

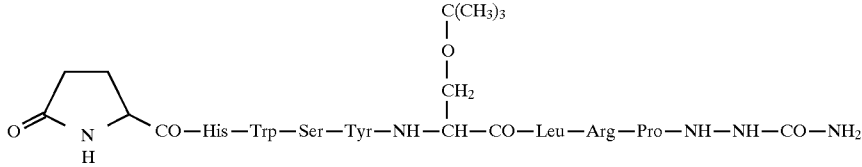

(U.S. Pat. No. 4,100,274, Japanese Patent Unexamined Publication No. 136172/1977);

(f) Nafarelin
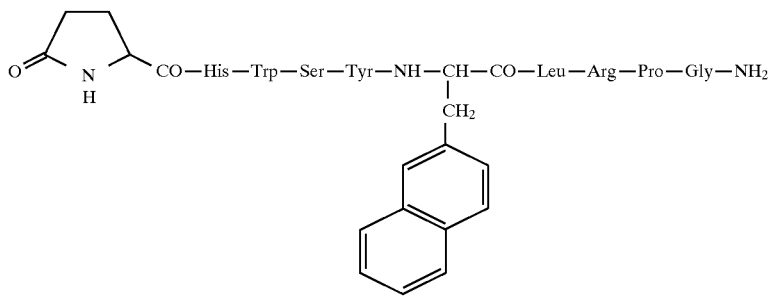
(U.S. Pat. No. 4,234,571, Japanese Patent Unexamined Publication Nos. 164663/1980, 264498/1988 and 25794/1989;
(g) Histrelin
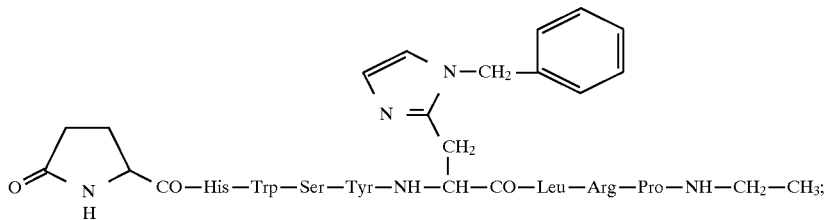
(h) Deslorelin
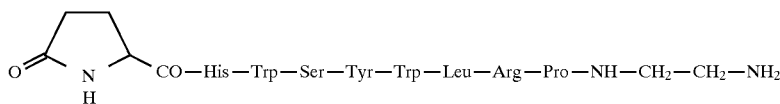
(U.S. Pat. Nos. 4,569,967 and 4,218,439);
(i) Meterelin
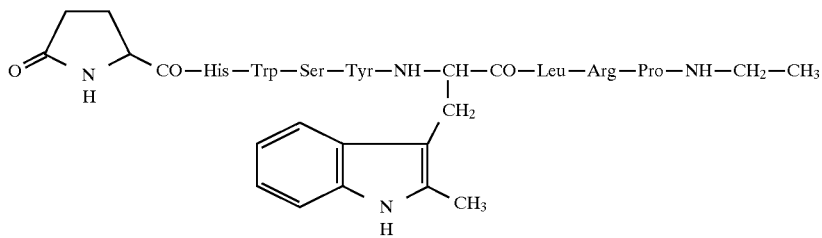
(WO9118016);
(j) Lecirelin
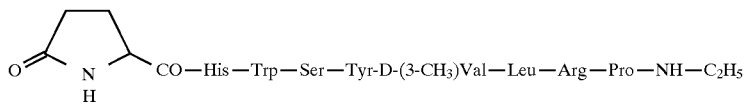
(Belgium Patent No. 897455, Japanese Patent Unexamined Publication No. 59654/1984).

In the above-described formulae (c) to (j), an amino acid which corresponds to $R_3$ in the formula (I) is of D-configuration.

Peptide (I) or a salt thereof is especially preferably leuprorelin or leuprorelin acetate.

Examples of the LH-RH antagonists include those disclosed in U.S. Pat. Nos. 4,086,219, 4,124,577, 4,253,997 and 4,317,815, or a peptide represented by the formula:

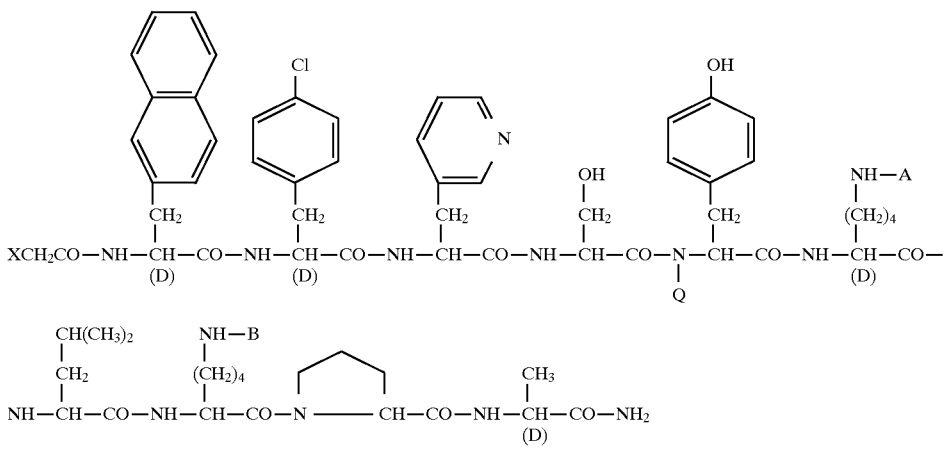

wherein X represents hydrogen atom or tetrahydrofurylcarboxamide; Q represents hydrogen atom or methyl; A represents nicotinoyl or N,N'-diethylamidino; B represents isopropyl or N,N'-diethylamidino; (hereafter also referred to as peptide (II)) or a salt thereof.

With respect to the formula (II), X is preferably tetrahydrofurylcarboxamide, more preferably (2S)-tetrahydrofurylcarboxamide. Also, A is preferably nicotinoyl; B is preferably isopropyl.

When peptide (II) has one or more kinds of asymmetric carbon atoms, two or more optical isomers are present. Such optical isomers and mixtures thereof are also included in the scope of the present invention.

Peptide (II) or a salt thereof can be produced by per se known methods. Such methods include the methods described in Japanese Patent Unexamined Publication No. 101695/1991 and the Journal of Medicinal Chemistry, Vol. 35, p. 3942 (1992) and other publications, and similar methods.

The salt of peptide (II) is preferably a pharmacologically acceptable salt. Such salts include salts formed with inorganic acids (e.g., hydrochloric acid, sulfuric acid, nitric acid), organic acids (e.g., carbonic acid, bicarbonic acid, succinic acid, acetic acid, propionic acid, trifluoroacetic acid) etc. More preferably, the salt of peptide (II) is a salt formed with an organic acid (e.g., carbonic acid, bicarbonic acid, succinic acid, acetic acid, propionic acid, trifluoroacetic acid), with greater preference given to a salt formed with acetic acid. These salts may be mono- through tri-salts.

Preferable examples of peptide (II) or a salt thereof are given below.

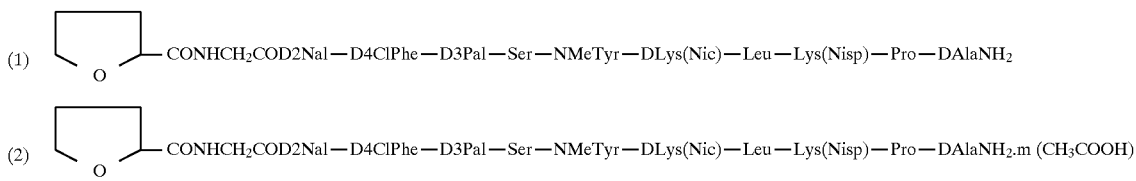

wherein m represents a real number of 1 to 3.

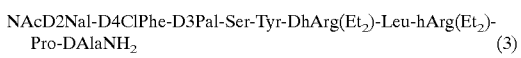

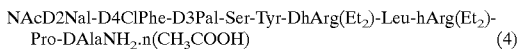

wherein n represents a real number of 1 to 3.

Peptide (II) or a salt thereof is especially preferably (1) or (2) above.

Examples of a physiologically active peptides include insulin, somatostatin, somatostatin derivative (Sandostatin; see U.S. Pat. Nos. 4,087,390, 4,093,574, 4,100,117 and 4,253,998), growth hormones, prolactin, adrenocorticotropic hormone (ACTH), ACTH derivatives (e.g., ebiratide), melanocyte-stimulating hormone (MSH), thyrotropin-releasing hormone [represented by the structural formula (Pyr)Glu-His-ProNH$_2$, hereinafter also referred to as TRH] and salts and derivatives thereof (see Japanese Patent Unexamined Publication Nos. 121273/1975 and 116465/1977), thyroid-stimulating hormone (TSH), luteinizing hormone (LH), follicle-stimulating hormone (FSH), vasopressin, vasopressin derivative [desmopressin, see Folia Endocrinologica Japonica, Vol. 54, No. 5, pp. 676–691 (1978)], oxytocin, calcitonin, parathyroid hormone (PTH), glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Publication No. 31567), endorphin, kyotorphin, interferons (e.g., α-, β- and γ-interferons), interleukins (e.g., 1, 2, 3, 4, 5, 6, 7, 8, 9, 10, 11 and 12), tuftsin, thymopoietin, thymosin, thymostimulin, thymic humoral factor (THF), blood thymic factor (FTS) and derivative thereof (see U.S. Pat. No. 4,229,438), other thymic factors [Igaku no Ayumi, Vol. 125, No. 10, pp. 835–843 (1983)], tumor necrosis factor (TNF), colony-stimulating factors (e.g., CSF, GCSF, GMCSF, MCSF), motilin, dynorphin, bombesin, neurotensin, caerulein, bradykinin, urokinase, asparaginase, kallikrein, substance P, insulin-like growth factors (IGF-I, IGF-II), nerve growth factor (NGF), cell growth factors (e.g., EGF, TGF-α, TGF-β, PDGF, acidic FGF, basic FGF), bone morphogenic factor (BMP), nerve nutrition factors (e.g., NT-3, NT-4, CNTF, GDNF, BDNF), blood coagulation factors VIII and IX, lysozyme chloride, polymixin B, colistin, gramicidin, bacitracin, erythropoietin (EPO), thrombopoietin (TPO), and endothelin-antagonistic peptides (see European Patent Publication Nos. 436189, 457195 and 496452, and Japanese Patent Unexamined Publication Nos. 94692/1991 and 130299/1991).

Examples of the antitumor agents include bleomycin, methotrexate, actinomycin D, mitomycin C, binblastin sulfate, bincrystin sulfate, daunorubicin, adriamycin, neocartinostatin, cytosinearabinoside, fluorouracil, tetrahydrofuryl-5-fluorouracil, krestin, Picibanil, lentinan, levamisole, Bestatin, azimexon, glycyrrhizin, polyI:C, polyA:U and polyICLC.

Examples of the antibiotics include gentamicin, dibekacin, Kanendomycin, lividomycin, tobramycin, amikacin, fradiomycin, sisomycin, tetracycline hydrochloride, oxytetracycline hydrochloride, rolitetracycline, doxycycline hydrochloride, ampicillin, piperacillin, ticarcillin, cefalothin, cefaloridine, cefotiam, cefsulodin, cefmenoxime, cefmetazole, cefazolin, cefotaxime, cefoperazon, ceftizoxime, mochisalactam, thienamycin, sulfazecin and aztreonam.

Examples of the antipyretic agents, analgesics and anti-inflammatory agents include salicylic acid, sulpyrine, flufenamic acid, diclofenac, indomethacin, morphine, pethidine hydrochloride, levorphanol tartrate and oxymorphone.

Examples of the antitussive expectorants include ephedrine hydrochloride, methylephedrine hydrochloride, noscapine hydrochloride, codeine phosphate, dihydrocodeine phosphate, allocramide hydrochloride, clofedanol hydrochloride, picoperidamine hydrochloride, chloperastine, protokylol hydrochloride, isoproterenol hydrochloride, sulbutamol sulfate and terbutaline sulfate.

Examples of the sedatives include chlorpromazine, prochlorperazine, trifluoperazine, atropine sulfate and methylscopolamine bromide.

Examples of the muscle relaxants include pridinol methanesulfonate, tubocurarine chloride and pancuronium bromide.

Examples of the antiepileptics include phenytoin, ethosuximide, acetazolamide sodium and chlordiazepoxide.

Examples of the antiulcer agents include metoclopramide and histidine hydrochloride.

Examples of the antidepressants include imipramine, clomipramine, noxiptiline and phenerdine sulfate.

Examples of the anti-allergic agents include diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride.

Examples of the cardiotonics include trans-paioxocamphor, theophyllol, aminophylline and etilefrine hydrochloride.

Examples of the antiarrhythmic agents include propranol, alprenolol, bufetolol and oxprenolol.

Examples of the vasodilators include oxyfedrine hydrochloride, diltiazem, tolazoline hydrochloride, hexobendine and bamethan sulfate.

Examples of the hypotensive diuretics include hexamethonium bromide, pentolinium, mecamylamine hydrochloride, ecarazine hydrochloride and clonidine.

Examples of the antidiabetics include glymidine sodium, glipizide, fenformin hydrochloride, buformin hydrochloride and metformin.

Examples of the antihyperlipidemic agents include pravastatin sodium, simvastatin, clinofibrate, clofibrate, simfibrate and bezafibrate.

Examples of the anticoagulants include heparin sodium.

Examples of the hemolytics include thromboplastin, thrombin, menadione sodium hydrogen sulfite, acetomenaphthone, ε-aminocaproic acid, tranexamic acid, carbazochrome sodium sulfonate and adrenochrome monoaminoguanidine methanesulfonate.

Examples of the antituberculosis agents include isoniazid, ethambutol and p-aminosalicylic acid.

Examples of the hormones include predonizolone, predonizolone sodium phosphate, dexamethasone sodium sulfate, betamethasone sodium phosphate, hexestrol phosphate, hexestrol acetate and methimazole.

Examples of the narcotic antagonists include levallorphan tartrate, nalorphine hydrochloride and naloxone hydrochloride.

Examples of the bone resorption suppressors include ipriflavone.

Examples of the osteogenesis promoters include polypeptides such as BMP, PTH, TGF-β and IGF-1, and (2R,4S)-(-)-N-[4-(diethoxyphosphorylmethyl)phenyl]-1,2,4,5-tetrahydro-4-methyl-7,8-methylenedioxy-5-oxo-3-benzothiepine-2-carboxamide and 2-(3-pyridyl)-ethane-1,1-diphosphonic acid.

Examples of the angiogenesis suppressors include angiogenesis-suppressing steroid [see Science, Vol. 221, p. 719 (1983)], fumagillin (see European Patent Publication No. 325199) and fumagillol derivatives (see European Patent Publication Nos. 357061, 359036, 386667 and 415294).

The physiologically active substance may be used as such or as a pharmacologically acceptable salt (e.g., salts formed with inorganic acids such as hydrochloric acid, sulfuric acid and nitric acid, and salts formed with organic acids such as carbonic acid and succinic acid, when the physiologically active substance has a basic group such as the amino group; salts formed with inorganic bases exemplified by alkali metals such as sodium and potassium, salts formed with organic base compounds exemplified by organic amines such as triethylamine, and basic amino acids such as arginine, when the physiologically active substance has an acidic group such as the carboxy group).

In the present invention, the physiologically active substance is preferably a physiologically active peptide, more preferably LH-RH or an analog thereof, still more preferably leuprorelin or leuprorelin acetate.

As a biodegradable polymer, preferably used is one having a free terminal carboxyl group.

A biodegradable polymer having a free terminal carboxyl group is a biodegradable polymer wherein the number-average molecular weight based on GPC measurement and the number-average molecular weight based on terminal group quantitation almost agree with each other.

The number-average molecular weight based on terminal group quantitation is calculated as follows:

About 1 to 3 g of the biodegradable polymer is dissolved in a mixed solvent of acetone (25 ml) and methanol (5 ml), and the solution is quickly titrated with a 0.05N alcoholic solution of potassium hydroxide while stirring at room temperature (20° C.) with phenolphthalein as an indicator to determine the carboxyl group content; the number-average molecular weight is calculated from the following equation:

Number-average molecular weight based on terminal group quantitation=20000×A/B

A: Weight mass (g) of biodegradable polymer

B: Amount (ml) of the 0.05N alcoholic solution of potassium hydroxide added until titration end point is reached For example, in the case of a polymer having a free terminal carboxyl group and which is synthesized from one or more α-hydroxy acids by catalyst-free dehydration condensation polymerization, the number-average molecular weight based on GPC measurement and the number-average molecular weight based on terminal group quantitation almost agree with each other. On the other hand, in the case of a polymer having substantially no free terminal carboxyl groups and which is synthesized from a cyclic dimer by ring-opening polymerization using a catalyst, the number-average molecular weight based on terminal group quantitation is significantly higher than that based on GPC measurement. This difference makes it possible to clearly differentiate a polymer having a free terminal carboxyl group from a polymer having no free terminal carboxyl group.

While the number-average molecular weight based on terminal group quantitation is an absolute value, that based on GPC measurement is a relative value that varies depending on various analytical conditions (e.g., kind of mobile phase, kind of column, reference substance, slice width chosen, baseline chosen etc.); it is therefore difficult to have an absolute numerical representation of these two values. However, the description that the number-average molecular weights based on GPC measurement and terminal group quantitation almost agree means that the latter falls within the range from about 0.4 to about 2 times, preferably from about 0.5 to about 2 times, and more preferably from about 0.8 to about 1.5 times, of the former. Also, the description that the number-average molecular weight based on terminal group quantitation is significantly higher than that based on GPC measurement means that the former is about 2 times or more greater than the latter.

Examples of the biodegradable polymers having a free terminal carboxyl group include homopolymers and copolymers synthesized from one or more α-hydroxy acids (e.g., glycolic acid, lactic acid, hydroxybutyric acid), hydroxydicarboxylic acids (e.g., malic acid), hydroxytricarboxylic acids (e.g., citric acid) etc. by catalyst-free dehydration condensation polymerization, mixtures thereof, poly-α-cyanoacrylates, polyamino acids (e.g., poly-γ-benzyl-L-glutamic acid) and maleic anhydride copolymers (e.g., styrene-maleic acid copolymers).

With respect to the above-described biodegradable polymer, polymerization may be of the random, block or graft type. When the above-mentioned α-hydroxy acids, hydroxydicarboxylic acids and hydroxytricarboxylic acids have an optical active center in their molecular structures, they may be of the D-, L- or DL-configuration.

The biodegradable polymer having a free terminal carboxyl group is preferably (1) a lactic acid/glycolic acid polymer (including homopolymers such as polylactic acid and polyglycolic acid, and copolymer of lactic acid and glycolic acid) or (2) a biodegradable polymer consisting of a mixture of (A) a copolymer of a glycolic acid and a hydroxycarboxylic acid represented by the formula:

$$\text{HO}-\underset{\underset{\text{R}}{|}}{\text{CH}}-\text{COOH} \qquad (III)$$

wherein R represents an alkyl group having 2 to 8 carbon atoms, and (B) a polylactic acid.

When the biodegradable polymer used is a lactic acid/glycolic acid polymer, its composition ratio (lactic acid/glycolic acid) (mol %) is preferably about 100/0 to about 40/60, more preferably about 90/10 to about 50/50.

The weight-average molecular weight of the above-described lactic acid/glycolic acid polymer is preferably about 5,000 to about 25,000, more preferably about 7,000 to about 20,000.

The degree of dispersion (weight-average molecular weight/number-average molecular weight) of the lactic acid/glycolic acid polymer is preferably about 1.2 to about 4.0, more preferably about 1.5 to about 3.5.

The above-described lactic acid/glycolic acid polymer can be produced by a known process, such as that described in Japanese Patent Unexamined Publication No. 28521/1986.

The decomposition/elimination rate of a lactic acid/glycolic acid polymer varies widely, depending on composition or molecular weight. Drug release duration can be extended by lowering the glycolic acid ratio or increasing the molecular weight, since decomposition/elimination is usually delayed as the glycolic acid ratio decreases. Conversely, drug release duration can be shortened by increasing the glycolic acid ratio or decreasing the molecular weight. To obtain a long-term (e.g., 1–4 months) sustained-release preparation, it is preferable to use a lactic acid/glycolic acid polymer whose composition ratio and weight-average molecular weight fall in the above-described ranges. With a lactic acid/glycolic acid polymer that decomposes more rapidly than that whose composition ratio and weight-average molecular weight fall in the above ranges, initial burst is difficult to suppress. On the contrary, with a lactic acid/glycolic acid polymer that decomposes more slowly than that whose composition ratio and weight-average molecular weight fall in the above ranges, it is likely that no effective amount of drug is released during some period.

With respect to the formula (III) above, the straight-chain or branched alkyl group represented by R, which has 2 to 8 carbon atoms, is exemplified by ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl. Preferably, a straight-chain or branched alkyl group having 2 to 5 carbon atoms is used. Such alkyl groups include ethyl, propyl, isopropyl, butyl and isobutyl. More preferably, R is ethyl.

The hydroxycarboxylic acid represented by the formula (III) is exemplified by 2-hydroxybutyric acid, 2-hydroxyvaleric acid, 2-hydroxy-3-methylbutyric acid, 2-hydroxycaproic acid, 2-hydroxyisocaproic acid and 2-hydroxycapric acid, with preference given to 2-hydroxybutyric acid, 2-hydroxyvaleric acid, 2-hydroxy-3-methylbutyric acid and 2-hydroxycaproic acid, with greater preference given to 2-hydroxybutyric acid. Although the hydroxycarboxylic acid may be of the D-, L- or D,L-configuration, it is preferable to use a mixture of the D- and L-configurations wherein the ratio of the D-/L-configuration (mol %) preferably falls within the range from about 75/25 to about 25/75, more preferably from about 60/40 to about 40/60, and still more preferably from about 55/45 to about 45/55.

With respect to the copolymer of glycolic acid and a hydroxycarboxylic acid represented by the formula (III) (hereinafter referred to as glycolic acid copolymer (A)), polymerization may be of random, block or graft type. A random copolymer is preferred.

The hydroxycarboxylic acid represented by the formula (III) may be a mixture of one or more kinds in a given ratio.

With respect to the composition ratio of glycolic acid and the hydroxycarboxylic acid represented by the formula (III) in glycolic acid copolymer (A), it is preferable that glycolic acid account for about 10 to about 75 mol % and hydroxycarboxylic acid for the remaining portion. More preferably, glycolic acid accounts for about 20 to about 75 mol %, and still more preferably about 40 to about 70 mol %. The weight-average molecular weight of the glycolic acid copolymer is normally about 2,000 to about 50,000, preferably about 3,000 to about 40,000, and more preferably about 8,000 to about 30,000. The degree of dispersion (weight-average molecular weight/number-average molecular weight) of the glycolic acid copolymer is preferably about 1.2 to about 4.0, more preferably about 1.5 to about 3.5.

The above-described glycolic acid copolymer (A) can be produced by a known process, such as that described in Japanese Patent Unexamined Publication No. 28521/1986.

Although the above-described polylactic acid (B) may be of the D- or L-configuration or a mixture thereof, it is preferable that the ratio of the D-/L-configuration (mol %) falls within the range from about 75/25 to about 20/80. The ratio of the D-/L-configuration (mol %) is more preferably about 60/40 to about 25/75, and still more preferably about 55/45 to about 25/75. The weight-average molecular weight of said polylactic acid is preferably about 1,500 to about 30,000, more preferably about 2,000 to about 20,000, and still more preferably about 3,000 to about 15,000. Also, the degree of dispersion of the polylactic acid is preferably about 1.2 to about 4.0, more preferably about 1.5 to about 3.5.

For producing a polylactic acid, two methods are known: ring-opening polymerization of lactide, a dimer of lactic acid, and dehydration condensation polymerization of lactic acid. For obtaining a polylactic acid of relatively low molecular weight for the present invention, direct dehydration condensation polymerization of lactic acid is preferred. Such a method, for example, can be carried out in accordance with the method described in Japanese Patent Unexamined Publication No. 28521/1986, or a method similar thereto.

Glycolic acid copolymer (A) and polylactic acid (B) are used in a mixture wherein the (A)/(B) ratio (% by weight) falls within the range from about 10/90 to about 90/10. The mixing ratio (% by weight) is preferably about 20/80 to about 80/20, and more preferably about 30/70 to about 70/30. If either component (A) or (B) is in excess, the preparation obtained shows a drug release pattern not much different from that obtained with the use of component (A) or (B) alone; the linear release pattern which is obtainable with the mixed base cannot be expected in the last stage of drug release. Although the decomposition/elimination rate of glycolic acid copolymer (A) and polylactic acid varies widely, depending on molecular weight or composition, drug release duration can be extended by increasing the molecular weight of polylactic acid mixed or lowering the mixing ratio (A)/(B), since the decomposition/elimination rate of glycolic acid copolymer (A) is usually higher. Conversely, drug release duration can be shortened by decreasing the molecular weight of polylactic acid mixed or increasing the mixing ratio (A)/(B). Drug release duration can also be adjusted by altering the kind and content ratio of hydroxycarboxylic acid represented by the formula (III).

A biodegradable polymer having a free terminal carboxyl group is more preferably a lactic acid/glycolic acid polymer. Especially, a lactic acid/glycolic acid polymer having a composition ratio (lactic acid/glycolic acid) (mol %) of 100/0 is a polylactic acid. Microspheres produced by using a polylactic acid are able to release a physiologically active substance stably for a long term as long as about 3 months or more. Therefore, a biodegradable polymer having a free terminal carboxyl group is still more preferably a polylactic acid.

In the present invention, a w/o/w emulsion and an o/w emulsion are produced by obtaining respectively (i) a w/o emulsion with an aqueous solution, a dispersion or a suspension of a physiologically active substance as an internal aqueous phase and an organic solvent solution of a biodegradable polymer as an oil phase, or (ii) an oil phase produced by dissolving or dispersing a physiologically active substance in an organic solvent solution of a biodegradable polymer; adding (i) or (ii) to water (external aqueous phase); and dispersing and emulsifying.

The above-described (i), i.e. a w/o emulsion with an aqueous solution, a dispersion or a suspension of a physiologically active substance as an internal aqueous phase and an organic solvent solution of a biodegradable polymer as an oil phase is produced in the following manner.

First, the physiologically active substance is dissolved, dispersed or suspended in water to yield an internal aqueous phase. The physiologically active substance concentration in an aqueous solution, a dispersion or a suspension is, for example, 0.001 to 90% (w/w), preferably 0.01 to 80% (w/w).

Although varying depending on kind of a physiologically active substance, desired pharmacological action, duration of action and other factors, the amount of a physiologically active substance to be used is normally about 0.01 to about 50% (w/w), preferably about 0.1 to about 40% (w/w), and more preferably about 1 to about 30% (w/w), relative to a biodegradable polymer.

To facilitate entrapment of a physiologically active substance in microspheres, a drug-retaining substance such as gelatin, agar, sodium alginate, polyvinyl alcohol, a basic amino acid (e.g., arginine, histidine, lysine) and the like may be added in an internal aqueous phase, if necessary. The amount of a drug-retaining substance added is normally 0.01 to 10 times by weight that of the physiologically active substance.

The internal aqueous phase may be once freeze dried to yield a powder, which may be dissolved in water to an appropriate concentration.

Separately, the biodegradable polymer is dissolved in an organic solvent to produce an oil phase. Examples of the organic solvents include halogenated hydrocarbons (e.g., dichloromethane, chloroform, chloroethane, trichloroethane, carbon tetrachloride), fatty acid esters (e.g., ethylacetate, butylacetate), and aromatic hydrocarbons (e.g. benzene, toluene, xylene), with preference given to dichloromethane.

Although varying depending on kind and molecular weight of the biodegradable polymer and kind of the organic solvent, the biodegradable polymer concentration in the organic solvent is normally 0.01 to 90% (w/w), preferably 0.01 to 70% (w/w). It is recommended that the biodegradable polymer be dissolved so that no portion remains undissolved.

To the thus-obtained organic solvent solution of a biodegradable polymer (oil phase), the above-described aqueous solution, dispersion or suspension of a physiologically active substance (internal aqueous phase) is added, followed by dispersion and emulsification using a homomixer or the like, to yield a w/o emulsion.

The above-described (ii), i.e. the oil phase produced by dissolving or dispersing a physiologically active substance in an organic solvent solution of a biodegradable polymer, is produced in the following manner.

First, an organic solvent solution of a biodegradable polymer is produced. As the organic solvent, use is made of substantially the same one that is used in producing the above-described w/o emulsion. The biodegradable polymer concentration in the organic solvent solution varies depending on molecular weight of the biodegradable polymer and kind of the organic solvent but is normally about 0.01 to about 70% (w/w), preferably about 1 to about 60% (w/w).

Next, a physiologically active substance is dissolved or suspended in an organic solvent solution of a biodegradable polymer, to yield an oil phase.

The amount of a physiologically active substance to be used is selected so that the ratio of the physiologically active substance to a biodegradable polymer is the same as in the case of producing the above-described w/o emulsion (i). The physiologically active substance to be used in (ii) is preferably insoluble or sparingly soluble in water.

Next, the above-described (i) w/o emulsion or (ii) oil phase is then added to an external aqueous phase and dispersed and emulsified using a homomixer or the like, to yield a w/o/w emulsion or a o/w emulsion, respectively. The external aqueous phase is used in a volume 1 to 10000 times, preferably 10 to 2000 times, and more preferably 50 to 500 times, that of the above-described (i) or (ii). The external aqueous phase is normally supplemented with an emulsifier. Any emulsifier can be used, as long as it generally produces a stable w/o/w emulsion or o/w emulsion. Such emulsifiers include anionic surfactants, nonionic surfactants, polyoxyethylene castor oil derivatives, polyvinylpyrrolidone, polyvinyl alcohol, carboxymethyl cellulose, lecithin, gelatin and hyarulonic acid, with preference given to polyvinyl alcohol. The emulsifier concentration in the external aqueous phase is normally 0.001 to 20% (w/w), preferably 0.01 to 10% (w/w), and more preferably 0.05 to 5% (w/w).

The thus-obtained w/o/w emulsion or o/w emulsion (hereinafter, these are also referred to briefly as emulsion) is subjected to an in-water drying method to remove an organic solvent contained in these emulsions to yield microspheres.

Preferable various conditions in carrying out the in-water drying method are described below in detail.

The relation between an external aqueous phase and microspheres is represented by, for example, the relation of the volume of the external aqueous phase and the amount of microspheres (total weight amount of a physiologically active substance, a drug-retaining substance and a biodegradable polymer), and the amount of microspheres per $m^3$ of an external aqueous phase is normally about 0.1 to about 500 kg, preferably about 0.5 to about 100 kg, and more preferably about 1.0 to about 20 kg.

In-water drying method is conducted in an appropriate container, preferably a tight closed container whose inside is separated from ambient conditions.

The relation between a container and an external aqueous phase is represented by, for example, the relation of the volume of the external aqueous phase and the area of the external aqueous phase in contact with the gas phase. The square root of the area (unit: $m^2$) of liquid surface in contact with the gas phase, per the cube root of the volume (unit: $m^3$) of the external aqueous phase, is about 0.2 to about 4.5, preferably about 0.5 to about 3.0.

Also, depending on container size and shape, the amount of microspheres in the external aqueous phase per $m^2$ of liquid surface in contact with the gas phase is preferably about 0.01 to about 7,000 kg, more preferably about 0.02 to about 100 kg, and still more preferably about 0.05 to about 20 kg.

The emulsion is preferably fluidized. Fluidization of the emulsion can be achieved by circulation or stirring. For example, circulation is achieved by aspirating a portion of the emulsion from the container's bottom and returning it from the container's upper portion into the container via a pipe, normally using a pump. Also, stirring is achieved by means of stirring in reactors used for ordinary chemical synthesis etc., i.e., using a stirring blade or magnetic stirrer. In this case, it is recommended that the emulsion in the container be uniformly fluidized.

The degree of circulation or stirring is represented by the replacement frequency of an emulsion. The replacement frequency is expressed by the reciprocal of mean residence time. Specifically, the replacement frequency is expressed by dividing the amount of circulating liquid per minute by the amount of an emulsion in the container when an emulsion is circulated by using a pump. When an emulsion is stirred, the replacement frequency of the emulsion is expressed by dividing the mean angular velocity of the emulsion by $2\pi$. In the in-water drying method of the present invention, the replacement frequency of an emulsion is about 0.01 to about 10 times/minute, preferably about 0.1 to about 10 times/minute, and more preferably about 0.5 to about 10 times/minute.

A gas is preferably allowed to be present above the liquid surface of the emulsion. Said gas may be any one, as long as it does not affect the in-water drying method, such gases including air, carbon dioxide gas, nitrogen gas, argon gas and helium gas.

Since the gas above the liquid surface of an emulsion contains an organic solvent evaporated from the emulsion, it is desirably replaced with an organic solvent-free fresh one by sequential removal of portions thereof.

Gas replacement is achieved by, for example, blowing a gas toward the liquid surface. The gas used for blowing is normally of the same kind as the gas above the liquid surface of an emulsion. For example, the gas is blown to the vicinity of the liquid surface from one to several holes of about 0.2 to about 1.5 cm in inside diameter at a flow rate of about 10 to about 1,000 liters/minute, preferably about 50 to about 500 liters/minute, and more preferably about 100 to about 400 liters/minute. Gas pressure is, for example, set at about 0.3 to about 4.0 $kg/cm^2$, preferably about 0.5 to about 3.0 $kg/cm^2$.

Also, the rate of gas transfer near the liquid surface of an emulsion is about 0.1 to about 300 m/second, preferably about 10 to about 200 m/second, and more preferably about 50 to about 150 m/second.

Gas replacement is conducted so that the gas replacement frequency in the container is not less than about 0.5 times/minute, preferably about 0.5 to about 10 times/minute, and more preferably about 1 to about 10 times/minute.

By employing the above-described various conditions, in-water drying method is normally completed in a short time of about 0.5 to about 5 hours.

The microspheres thus obtained are recovered via centrifugation, sieving or the like, after which an aggregation inhibitor such as a sugar, sugar alcohol or inorganic salt, preferably mannitol or sorbitol, is optionally added to prevent mutual aggregation of microspheres, which is subjected to freeze drying.

The mixing ratio (weight ratio) of microspheres and aggregation inhibitor is normally 50:1 to 1:1, preferably 20:1 to 1:1, and more preferably 10:1 to 5:1.

The manner of adding the aggregation inhibitor is not limitted as long as a method wherein microspheres and the aggregation inhibitor are mixed uniformly is employed. Such a method is exemplified by a method wherein microspheres are dispersed in an aqueous solution of an aggregation inhibitor.

Although microspheres of the present invention can be administered to the living body as they are, they can also be administered after shaping into various preparations.

Such preparations include injectable preparations, implants, oral preparations (e.g., powders, granules, capsules, tablets, syrups, emulsions, suspensions), nasal preparations and suppositories (e.g., rectal suppositories, vaginal suppositories).

These preparations can be produced by known methods in common use for pharmaceutical production.

For example, injectable preparations are prepared by dispersing microspheres in an aqueous dispersant or an oily dispersant.

Examples of the aqueous dispersant include a solution which is prepared by dissolving in distilled water an isotonizing agent (e.g., sodium chloride, glucose, D-mannitol, sorbitol, glycerol), a dispersing agent (e.g, Tween 80, HCO-50, HCO-60 (produced by Nikko Chemicals), carboxymethyl cellulose, sodium alginate), a preservative (e.g., benzyl alcohol, benzalkonium chloride, phenol), a soothing agent (e.g., glucose, calcium gluconate, procaine hydrochloride) etc. Examples of the oily dispersant include olive oil, sesame oil, peanut oil, soybean oil, corn oil, and middle-chain fatty acid glycerides.

The injectable preparations may be loaded into a chamber of a pre-filled syringe. Also, the above-described dispersants and microspheres may be loaded separately into a different chamber of Double-Chamber Pre-filled Syringe (DPS) which is a pre-filled syringe having two chambers.

An oral preparation can be produced by, for example, adding an excipient (e.g., lactose, sucrose, starch), a disintegrating agent (e.g., starch, calcium carbonate), a binder (e.g., starch, gum arabic, carboxymethyl cellulose, polyvinylpyrrolidone, hydroxypropyl cellulose) or a lubricant (e.g., talc, magnesium stearate, polyethylene glycol 6000) to microspheres, subjecting the mixture to compressive shaping, followed by coating to mask the taste or conferring an enteric or sustained-release property by a well-known method when necessary. Useful coating agents include hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (Rohm Company, West Germany, methacrylic acid-acrylic acid copolymer), and dyes such as titanium oxide and iron oxide red.

The nasal preparation may be solid, semi-solid or liquid. For example, a solid nasal preparation can be produced normally by adding an excipient (e.g., glucose, mannitol, starch, microcrystalline cellulose), a thickening agent (e.g., natural rubber, cellulose derivative, acrylic acid polymer) etc. to microspheres and mixing them, although microspheres as such may be used. A liquid nasal preparation can be produced in almost the same manner as for an injectable preparation. All these preparations may contain a pH regulator (e.g., carbonic acid, phosphoric acid, citric acid, hydrochloric acid, sodium hydroxide), an antiseptic (e.g., p-oxybenzoate, chlorobutanol, benzalkonium chloride) etc.

The suppository may be oily or aqueous; and solid, semi-solid or liquid. The suppository is produced normally by using oily bases, aqueous bases or aqueous gel bases. Such oily bases include glycerides of higher fatty acids [e.g., cacao fat, Witepsol-series products (Dynamite Nobel company)], moderate fatty acids [e.g., MIGLYOL-series products (Dynamite Nobel Company)], and vegetable oils (e.g., sesame oil, soybean oil, cottonseed oil). Aqueous bases include polyethylene glycols and propylene glycol. Aqueous gel bases include natural rubbers, cellulose derivatives, vinyl polymers and acrylic acid polymers.

Microspheres of the present invention are preferably used in the form of an injectable preparation.

The mean particle diameter of microcapsules in the present invention is chosen over the range in which the requirements concerning the degree of dispersion and needle passability are met when the microspheres are used in the form of an injectable suspension. For example, mean diameter falls within the range from about 1 to about 300 $\mu$m, preferably about 5 to about 100 $\mu$m.

The microspheres of the present invention and a preparation comprising the microspheres (hereafter, these are referred to briefly as a microsphere preparation) are of low toxicity and can be used safely.

Although varying depending on kind and content of a physiologically active substance as an active ingredient, dosage form, duration of a physiologically active substance release, subject animal species (e.g., warm-blooded mammals such as mice, rats, horses, bovines and humans), and purpose of administration, the dose of the microsphere preparation may be set at any level, as long as the active ingredient is effective. The dose of the preparation per administration can be chosen as appropriate over the range from about 1 mg to about 10 g, preferably from about 10 mg to about 2 g per adult (weight 50 kg) in terms of the weight of microspheres. When the microsphere preparation is an injectable preparation, the volume of the dispersant can be chosen as appropriate over the range from about 0.5 to about 3 ml.

Especially, when a physiologically active substance is, for example, peptide (I), (II), or a salt thereof, a microsphere preparation is useful as a preparation for treatment or prophylaxis of hormone-dependent diseases such as prostatic cancer, prostatic hypertrophy, breast cancer, endometriosis, myoma of the uterus, and neurogenic precocious puberty, or a contraceptive.

Especially, when a physiologically active substance in a microsphere preparation is peptide (I) or a salt thereof, the preparation is an injectable preparation, and the preparation is used as a preparation for treatment or prophylaxis of the above-described diseases, the dose of the preparation per administration in terms of peptide (I) or a salt thereof ranges preferably from about 1 to about 100 mg, more preferably from about 1 to about 10 mg per adult (weight 50 kg).

The present invention is hereinafter described in more detail by means of the following examples, comparative example, and experimental examples, which are not to be construed as limitative, as long as they fall within the scope of the present invention. Unless otherwise specified, % means % by weight.

EXAMPLE 1

In an eggplant type flask, 65.0 g of leuprorelin acetate and 10.3 g of gelatin were weighed and completely dissolved in 66 ml of water for injection. To this solution, 521.9 g of a lactic acid/glycolic acid copolymer [lactic acid/glycolic acid=75/25 (mol %), weight-average molecular weight: about 11,000] dissolved in 873.6 g of dichloromethane (methylene chloride) was added, followed by stirring and emulsification using the autominimixer for 10 minutes to yield a w/o emulsion.

After 150 liters of a 0.1% aqueous solution of polyvinyl alcohol (Gosenol EG40) (hereafter referred to as PVA solution) (external aqueous phase) was poured in a 200 liter tank, the above-described w/o emulsion was added to the solution, followed by stirring and emulsification to yield a w/o/w emulsion. The amount of the w/o emulsion actually poured in the tank was 99% or more while adhesion of the emulsion to the inside of the tank and a pipe was observed. The w/o/w emulsion was subjected to in-water drying for 3 hours under the conditions shown below.

Container size: 200 liters

Amount of gas phase: 50 liters

Amount of external aqueous phase: 150 liters

Amount of microspheres per $m^3$ of external aqueous phase: 4.0 kg

Amount of microspheres in external aqueous phase 1.2 kg per $m^2$ of liquid surface in contact with gas phase Square root of the area (unit: $m^2$) of liquid surface in contact with gas phase per cube root of the volume (unit: $m^3$) of external aqueous phase: 1.3

Replacement frequency of emulsion: 1.3 times/minute (200 liters/minute)

Gas transfer rate near liquid surface: 100 m/second

Replacement frequency of gas above liquid surface: 6 times/minute

Fluidization of an emulsion was conducted by circulation of an emulsion, i.e. taking a portion of an emulsion from the tank's bottom via a pipe and returning it to the upper portion of the liquid phase via a pipe using a pump. Also, fluidization of the gas near the liquid surface was conducted by blowing compressed air at a flow rate of 300 liters/minute at an angle of about 30 degrees to the liquid surface via a pipe of 6 mm in inside diameter from about 10 cm above the liquid surface.

After in-water drying, the obtained microspheres were recovered, followed by the addition of mannitol (94.1 g) and freeze drying, to yield microsphere powders.

EXAMPLE 2

To an aqueous solution of 0.5 g of thyrotropin-releasing hormone (TRH) in 0.2 g of water, a solution of 4.5 g of a lactic acid/glycolic acid copolymer [lactic acid/glycolic acid=75/25 (w/w), weight-average molecular weight: about 14000] in dichloromethane (4.9 ml) was added to yield a w/o emulsion.

The w/o emulsion was dispersed in 1 liter of a 0.1% PVA solution (external aqueous phase) to yield a w/o/w emulsion.

The w/o/w emulsion was subjected to in-water drying for 3 hours under the conditions shown below.

Container size: 2.5 liters

Amount of gas phase: 1.5 liters

Amount of external aqueous phase: 1 liter

Amount of microspheres per $m^3$ of external aqueous phase: 5 kg

Amount of microspheres in external aqueous phase: 0.09 kg per $m^2$ of liquid surface in contact with gas phase Square root of the area (unit: $m^2$) of liquid surface in contact with gas phase per cube root of the volume (unit: $m^3$) of external aqueous phase: 2.4

Replacement frequency of emulsion: 1.9 times/minute (mean angular velocity 3.8 π/minute)

Gas transfer rate near liquid surface: 100 m/second

Replacement frequency of gas above liquid surface: 5 times/minute

Fluidization of an emulsion was conducted by stirring an emulsion in the tank using a mechanical stirrer. Also, fluidization of the gas near the liquid surface was conducted by blowing nitrogen at a flow rate of 100 liters/minute at an angle of about 20 degrees to the liquid surface via a pipe of 3 mm in inside diameter from about 5 cm above the liquid surface.

After in-water drying, microspheres were then collected via centrifugation and freeze dried. By nitrogen blowing, the drug entrapment ratio in microspheres was increased by 4%, in comparison with microspheres prepared without nitrogen blowing.

EXAMPLE 3

In an eggplant type flask, 119.3 g of leuprorelin acetate and 18.7 g of gelatin were weighed and completely dissolved in 120 ml of water for injection. To this solution, 957.2 g of a lactic acid/glycolic acid copolymer [lactic acid/glycolic acid=75/25 (mol %), weight-average molecular weight: about 11,000] dissolved in 1602.8 g of dichloromethane was added, followed by stirring and emulsification using the autohomomixer for 10 minutes to yield a w/o emulsion.

After 200 liters of a 0.1% PVA solution (external aqueous phase) was poured in a 360 liter tank, the above-described w/o emulsion was added to the solution, followed by stirring and emulsification to yield a w/o/w emulsion. The amount of the w/o emulsion actually poured in the tank was 99% or more while adhesion of the emulsion to the inside of the tank and a pipe was observed.

The w/o/w emulsion was subjected to in-water drying for 3 hours under the conditions shown below.

Container size: 360 liters

Amount of gas phase: 160 liters

Amount of external aqueous phase: 200 liters

Amount of microspheres per $m^3$ of external aqueous phase: about 5.5 kg

Amount of microspheres in external aqueous phase: about 2.2 kg per $m^2$ of liquid surface in contact with gas phase Square root of the area (unit: $m^2$) of liquid surface in contact with gas phase per cube root of the volume (unit: $m^3$) of external aqueous phase: 1.2

Replacement frequency of emulsion: 1 time/minute (200 liters/minute)

Gas transfer rate near liquid surface 100 m/second

Replacement frequency of gas above liquid surface: 1.8 times/minute

Fluidization of an emulsion and fluidization of a gas were conducted in the same manner as in Example 1.

After in-water drying, the obtained microspheres were recovered, followed by the addition of mannitol (172.6 g) and freeze drying, to yield microsphere powders.

EXAMPLE 4

In an eggplant type flask, 86.7 g of leuprorelin acetate was weighed and completely dissolved in 100 ml of water for injection. To this solution, 765.1 g of a polylactic acid [weight-average molecular weight: about 14,000] dissolved in 1280 g of dichloromethane was added, followed by stirring and emulsification using the autohomomixer for 13.5 minutes to yield a w/o emulsion.

After 200 liters of a 0.1% PVA solution (external aqueous phase) was poured in a 360 liter tank, the above-described w/o emulsion was added to the solution, followed by stirring and emulsification to yield a w/o/w emulsion. The amount of the w/o emulsion actually poured in the tank was 99% or more while adhesion of the emulsion to the inside of the tank and a pipe was observed.

The w/o/w emulsion was subjected to in-water drying in the same manner as in Example 3 except that the amount of microspheres per $m^3$ of external aqueous phase was about 4.2 kg, and the flow rate of gas was 350 liters/minute.

After in-water drying, the obtained microspheres were recovered, followed by the addition of mannitol (134.3 g) and freeze drying, to yield microsphere powders.

EXAMPLE 5

In-water drying was conducted in the same manner as in Example 1 except that the replacement frequency of emulsion was 0.13 times/minute (20 liters/minute), to yield microspheres.

The microspheres were recovered, followed by the addition of mannitol (94.1 g) and freeze drying, to yield microsphere powders.

EXAMPLE 6

In-water drying was conducted in the same manner as in Example 1 except that fluidization of an emulsion was conducted by stirring an emulsion in a tank, and the replacement frequency of emulsion was 1.3 times/minute (200 liters/minute), to yield microspheres.

The microspheres were recovered, followed by the addition of mannitol (94.1 g) and freeze drying, to yield microsphere powders.

EXAMPLE 7

In-water drying gas conducted in the same manner as in Example 1 except that the replacement frequency of gas above liquid surface was 1.3 times/minute (200 liters/minute via a pipe of 12 mm in inside diameter), and the gas transfer rate near liquid surface was 15 m/second, to yield microspheres.

The microspheres were recovered, followed by the addition of mannitol (94.1 g) and freeze drying, to yield microsphere powders.

EXAMPLE 8

In an eggplant type flask, 80.5 g of leuprorelin acetate and 12.6 g of gelatin were weighed and completely dissolved in 80 ml of water for injection. To this solution, 646.1 g of a lactic acid/glycolic acid copolymer [lactic acid/glycolic acid=75/25 (mol %), weight-average molecular weight: about 11,000] dissolved in 1081.9 g of dichloromethane was added, followed by stirring and emulsification using the autohomomixer for 10 minutes to yield a w/o emulsion.

After 135 liters of a 0.1% PVA solution (external aqueous phase) was poured in a 300 liter tank, the above-described w/o emulsion was added to the solution, followed by stirring and emulsification to yield a w/o/w emulsion. The amount of the w/o emulsion actually poured in the tank was 99% or more while adhesion of the emulsion to the inside of the tank and a pipe was observed.

The w/o/w emulsion was subjected to in-water drying for 3 hours under the conditions shown below.

Container size: 300 liters

Amount of gas phase: 165 liters

Amount of external aqueous phase: 135 liters

Amount of microspheres per $m^3$ of external aqueous phase: about 5.5 kg

Square root of the area (unit: $m^2$) of liquid surface in contact with gas phase per cube root of the volume (unit: $m^3$) of external aqueous phase: 1.4

Replacement frequency of emulsion: 2.2 times/minute (300 liters/minute)

Gas transfer rate near liquid surface: 100 m/second

Replacement frequency of gas above liquid surface: 1.8 times/minute

Fluidization of an emulsion and fluidization of a gas were conducted in the same manner as in Example 1.

After in-water drying, the obtained microspheres were recovered using a centrifugal separator.

COMPARATIVE EXAMPLE

In-water drying was conducted in the same manner as in Example 8 except that the replacement frequency of emulsion was 0.8 times/minute (100 liters/minute), and blowing of compressed air was not conducted. The obtained microspheres were recovered.

EXPERIMENTAL EXAMPLE 1

Regarding microspheres and microsphere powders, obtained in Example 5, 6 and 7, solvent contents at completion of in-water drying and entrapment ratio of active ingredient at completion of freeze drying were respectively shown in Table 1.

TABLE 1

| Example No. | Solvent Content in Microspheres | Entrapment Ratio of Active Ingredient after Freeze Drying |
|---|---|---|
| 5 | 3000 ppm | 94% |
| 6 | 1000 ppm | 95% |
| 7 | 20000 ppm | 91% |

As is clear from Table 1, microspheres having low solvent contents and high entrapment ratio of active ingredient can be produced according to the method of the present invention.

EXPERIMENTAL EXAMPLE 2

Regarding microspheres obtained in Example 8 and Comparative Example, solvent contents at completion of in-water drying and workability in recovering were shown in Table 2.

TABLE 2

| | Solvent Content in Microspheres | Workability in Recovering |
|---|---|---|
| Example 8 | 1200 ppm | very good |
| Comparative Example | 40000 ppm | microsphere aggregation was observed and bad in workability |

As is clear from Table 2, microspheres having low solvent contents and excellent workability in recovering can be produced by blowing a gas to an emulsion in in-water drying.

According to the method of the present invention, the rate of solvent removal from microspheres in in-water drying is increased and the amount of solvent in microspheres can be reduced in a short time. And, it is possible to produce microspheres containing small amount of solvent and having a high entrapment ratio of the active ingredient.

Also, microspheres excellent in workability at the time of collection can be produced.

Further, microspheres produced by the method of the present invention are excellent in dispersibility and needle passability when they are used as a medicinal injectable preparation.

What we claim is:

1. A method of producing microspheres comprising a physiologically active substance and a biodegradable polymer, which comprises subjecting a w/o/w emulsion or o/w emulsion wherein said physiologically active substance is in an inner aqueous phase and said biodegradable polymer is in an external oil phase to an in-water drying method under the following conditions:

1) the amount of microspheres per $m^3$ in an external aqueous phase is about 0.1 to about 500 kg,
   2) the square root of the area (unit: $m^2$) of the liquid surface in contact with the gas phase is about 0.2 to about 4.5 per the cube root of the volume (unit: $m^3$) of the external aqueous phase,
   3) the w/o/w emulsion or o/w emulsion is replaced at a replacement frequency of about 0.01 to about 10 times/minute,
   4) a gas is blown toward the w/o/w emulsion or o/w emulsion so that the gas transfer rate near the liquid surface is about 10 to 300 m/second, and
   5) the gas is replaced at a replacement frequency of not less than about 0.5 times/minute.

2. The method according to claim 1, wherein the amount of microspheres per $m^3$ in the external aqueous phase is about 0.5 to about 100 kg.

3. The method accordingly to claim 1, wherein the square root of the area (unit: $m^2$) of the liquid surface in contact with the gas phase is about 0.5 to about 3.0 per the cube root of the volume (unit: $m^3$) of the external aqueous phase.

4. The method according to claim 1, wherein the physiologically active substance is a physiologically active peptide.

5. The method according to claim 1, wherein the physiologically active substance is an LH-RH agonist or an LH-RH antagonist.

6. The method according to claim 1, wherein the biodegradable polymer is a biodegradable polymer having a free terminal carboxyl group.

7. The method according to claim 1, wherein the biodegradable polymer is a lactic acid/glycolic acid polymer.

8. The method according to claim 1, wherein the gas transfer rate near the liquid surface is about 10 to about 200 m/second.

9. The method according to claim 1, wherein the gas transfer rate near the liquid surface is about 50 to about 150 m/second.

10. The method according to claim 7, wherein the composition ratio of a lactic acid/glycolic acid is from about 90/10 to about 50/50.

11. The method according to claim 1, wherein the physiologically active substance is a substance selected from the group consisting of LH-RH agonist, LH-RH antagonist, antitumor agent, antibiotic, antipyretic agent, analgesic, anti-inflammatory agent, antitussive expectorant, sedative, muscle relaxant, antiepileptic, antiulcer agent, antidepressant, anti-allergic agent, cardiotonic, antiarrhythmic agent, vasodilator, hypotensive diuretic, antidiabetic, antihyperlipidemic agent, anticoagulant, hemolytic, antituberculosis agent, hormone, narcotic antagonist, bone resorption suppressor, osteogenesis promoter and angiogenesis inhibitor.

12. The method according to claim 1, wherein the physiologically active substance is:

(1) a peptide represented by the formula:

$$(Pyr) Glu-R_1-Trp-Ser-R_2-R_3-R_4-Arg-Pro-R_5 \quad (I)$$

wherein $R_1$ represents His, Tyr, Trp or p-$NH_2$-Phe; $R_2$ represents Tyr or Phe; $R_3$ represents Gly or a D- amino acid residue; $R_4$ represents Leu, Ile or Nle; $R_5$ represents (a) Gly-NH—$R_6$ wherein $R_6$ is H or an alkyl group with or without a hydroxyl group or (b) NH—$R_7$ wherein $R_7$ is H, an alkyl group with or without an amino or a hydroxyl group, or (c) ureido (—NH—CO—$NH_2$); or (2) a peptide represented by the formula:

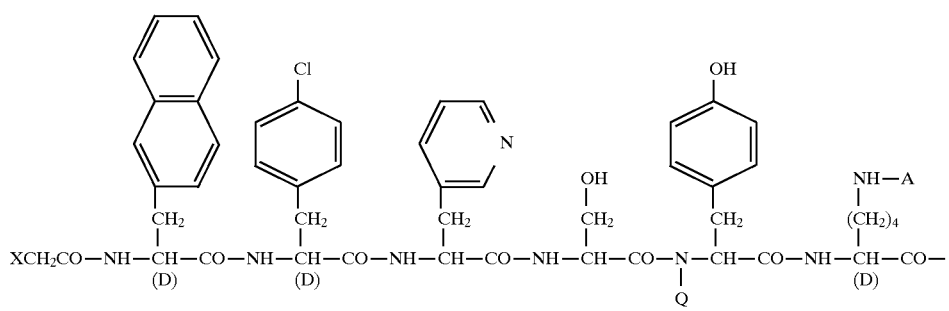

(II)

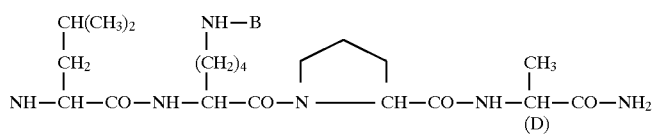

wherein X represents hydrogen atom or tetrahydrofurylcarboxamide; Q represents hydrogen atom or methyl; A represents nicotinoyl or N,N'-diethylamidino; B represents isopropyl or N,N'-diethylamidino; or a salt thereof.

13. The method according to claim 1, wherein the physiologically active substance is leuprorelin or leuprorelin acetate.

14. A method of producing microspheres comprising a physiologically active substance and a biodegradable polymer, which comprises subjecting a w/o/w emulsion or o/w emulsion wherein said physiologically active substance is in an inner aqueous phase and said biodegradable polymer in an external oil phase to an in-water-drying method under the following conditions:

1) the amount of microspheres per $m^3$ in an external aqueous phase is about 0.1 to about 500 kg,
2) the square root of the area (unit: $m^2$) of the liquid surface in contact with the gas phase is about 0.2 to about 4.5 per the cube root of the volume (unit: $m^3$) of the external aqueous phase,
3) the w/o/w emulsion or o/w emulsion is replaced at a replacement frequency of about 0.01 to about 10 times/minute,
4) a gas is blown toward the w/o/w emulsion or o/w emulsion so that the gas transfer rate near the liquid surface is about 10 to about 200 m/second, and
5) the gas is replaced at a replacement frequency of not less than about 0.5 times/minute, wherein the physiologically active substance is leuprorelin or leuprorelin acetate, and the biodegradable polymer is a lactic acid/glycolic acid polymer having a composition ratio of about 90/10 to 50/50.

* * * * *